United States Patent
Hasegawa et al.

[19]

[11] Patent Number: 6,094,975

[45] Date of Patent: Aug. 1, 2000

[54] HEATER CONTROL HAVING CAPABILITY OF RESTORING NORMAL HEATER POWER SUPPLY AFTER DETECTION OF ABNORMALITY

[75] Inventors: Jun Hasegawa; Yukihiro Yamashita, both of Kariya, Japan

[73] Assignee: Denso Corporation, Japan

[21] Appl. No.: 09/055,782

[22] Filed: Apr. 7, 1998

[30] Foreign Application Priority Data

Apr. 23, 1997 [JP] Japan ................................ 9-105962

[51] Int. Cl.[7] ............................ F02D 45/00; G01M 15/00

[52] U.S. Cl. ....................... 73/118.1; 73/23.32; 60/276; 701/109; 123/688

[58] Field of Search ....................... 73/118.1, 23.31, 73/23.32; 60/276, 277; 701/103, 104, 109; 123/688

[56] References Cited

U.S. PATENT DOCUMENTS

| | | | |
|---|---|---|---|
| 4,938,196 | 7/1990 | Hoshi et al. | 123/489 |
| 4,993,392 | 2/1991 | Tanaka et al. | 123/489 |
| 5,280,158 | 1/1994 | Matava et al. | 219/492 |
| 5,544,640 | 8/1996 | Thomas et al. | 73/23.32 |
| 5,637,786 | 6/1997 | Weber et al. | 73/23.32 |
| 5,656,190 | 8/1997 | Aoki | 219/505 |
| 5,701,877 | 12/1997 | Aoki | 123/697 |
| 5,752,493 | 5/1998 | Abe et al. | 123/686 |
| 5,758,492 | 6/1998 | Kato et al. | 60/277 |
| 5,771,688 | 6/1998 | Hasegawa et al. | 60/276 |
| 5,852,228 | 12/1998 | Yamashita et al. | 73/23.32 |
| 5,928,303 | 7/1999 | Sakai | 701/109 |
| 5,964,208 | 10/1999 | Yamashita et al. | 123/674 |

FOREIGN PATENT DOCUMENTS

| | | | |
|---|---|---|---|
| 3-165245 | 7/1991 | Japan | G01R 19/25 |
| 7-77546 | 3/1995 | Japan | G01N 27/12 |

*Primary Examiner*—George Dombroske
*Attorney, Agent, or Firm*—Nixon & Vanderhye PC

[57] ABSTRACT

In a system using a gas concentration sensor such as an A/F sensor having a heater, a microcomputer detects an abnormality in a heater power supply control. After the detection of abnormality, the computer reduces the electric power to the heater to a minimum and determines whether the heater has restored its normal operation. The power supply to the heater is stopped and returned to the normal power supply control when it is determined that the detected abnormality continues and discontinues during the reduced power supply period, respectively.

20 Claims, 9 Drawing Sheets

HEATER CONTROL HAVING CAPABILITY OF RESTORING NORMAL HEATER POWER SUPPLY AFTER DETECTION OF ABNORMALITY

CROSS REFERENCE TO RELATED APPLICATION

This application relates to and incorporates herein by reference Japanese patent application No. 9-105962 filed on Apr. 23, 1997.

BACKGROUND OF THE INVENTION

The present invention relates to an apparatus and method for controlling a heater provided in a gas concentration sensor for promoting activation of the gas concentration sensor.

Recently, there has been a demand for air-fuel ratio control for a vehicle-mounted engine, having enhanced control accuracy and lean mixture combustion in the engine. To meet those demands, a linear air-fuel ratio sensor (an oxygen responsive limit-current type A/F sensor) is used for detecting air-fuel ratio of air-fuel mixture gas supplied to the engine linearly over a wide air-fuel ratio zone. It is necessary to maintain the temperature of the sensor to a predetermined activation temperature in order to detect the air-fuel ratio (concentration of oxygen in exhaust gas) with high accuracy. For this purpose, the sensor is generally provided with a heater. The heater is controlled by an electric power supply control or by a feedback control for maintaining the heater temperature at a predetermined sensor activation temperature.

However, in the above heater control, it is likely that a heater abnormality is detected erroneously during operation of the sensor by an electric noise or a temporary electrical disconnection even while the heater control is the performed normally. Stopping the heater control in response to the detection of the heater abnormality will disable the air-fuel ratio feedback control using a highly accurate output signal of the sensor. Thus, it is necessary to restore the heater control to the normal operation when the abnormality of heater is temporary.

SUMMARY OF THE INVENTION

It is therefore an object of the present invention to provide a heater control for a gas concentration detection sensor capable of restoring a normal operation thereof when an abnormality of the sensor is temporary.

According to the present invention, after a detection of an abnormality in a heater and responsively disabling a heater power supply, a restoration of the heater power supply to a normal operative state is detected thereby to restore the heater control once disabled. In the case of a vehicle-mounted engine system using an air-fuel ratio sensor in an exhaust pipe, the sensor can be maintained at about 400–500° C. by exhaust gas of the engine even when the temperature of the sensor decreases due to abnormality or inoperativeness of the heater. Thus, sensor can be maintained in a semi-active state in which the sensor outputs a signal varying in accordance with presence/absence of oxygen in the exhaust emission. Therefore, it is possible to use the output signal of the sensor in the air-fuel ratio control even under the sensor semi-active state.

BRIEF DESCRIPTION OF THE DRAWINGS

Other objects, features and advantages of the present invention will become more apparent from the following detailed description when read with reference to the accompanying drawings. In the accompanying drawings.

DETAILED DESCRIPTION OF THE PREFERRED EMBODIMENT

Figure 1:
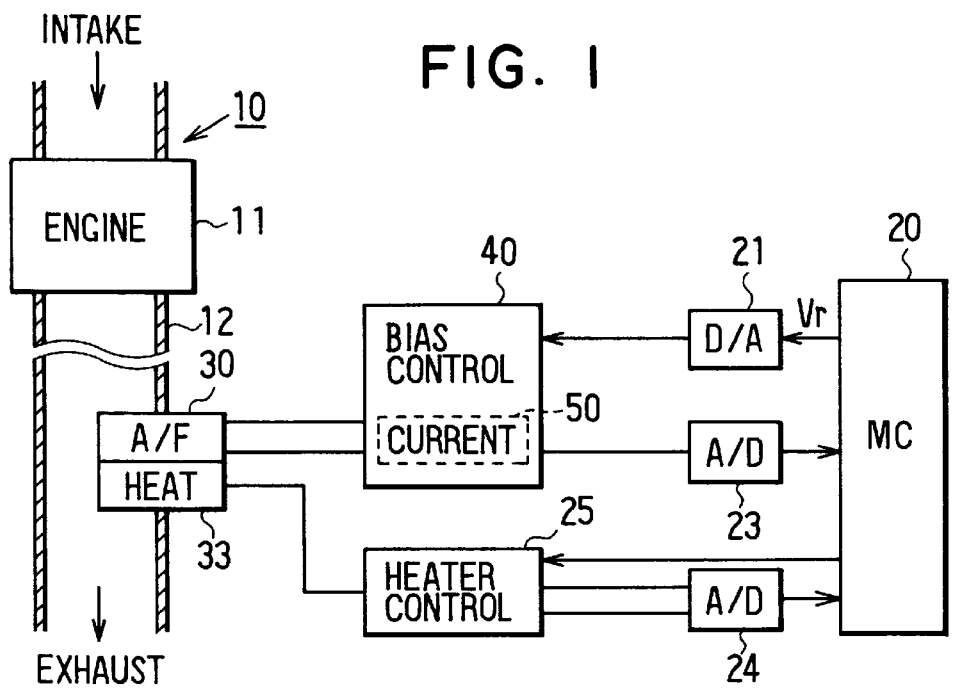
FIG. 1 is a block diagram showing a heater control apparatus in a gas concentration detection system according to the first embodiment of the present invention.

The present invention will be described in detail hereinbelow with reference to the first and second embodiments and modifications thereof shown in the drawings. It is to be noted that the following embodiments and modifications are directed to an oxygen concentration detection system which has a heater control and can be applied to an electronically controlled gasoline injection engine mounted on a vehicle.

First Embodiment

In FIG. 1 showing a block diagram of an air-fuel ratio detecting apparatus, an oxygen responsive air-fuel ratio (A/F) sensor 30 of a limit-current type is used. The A/F sensor 30 having a heater 33 is attached to an exhaust pipe 12 extending from an engine body 11 of an engine 10 and outputs a linear air-fuel ratio detection signal (sensor current signal) proportional to the concentration of oxygen in the exhaust with application of a voltage instructed by a microcomputer (MC computer) 20. The computer 20 is constructed, as is well known in the art, by a CPU for executing various kinds of processing, a ROM, a RAM, a back-up RAM, and the like to control a heater control circuit 25 and a bias control circuit 40 in accordance with predetermined control programs. The back-up RAM is constructed as a memory which can hold stored data even after turn-off of an electric power supply to the computer 20.

A bias instruction signal Vr outputted from the computer 20 is supplied to the bias control circuit 40 via a D/A converter 21. The output of the A/F sensor 30 corresponding to the air-fuel ratio (concentration of oxygen) is detected by a sensor current by a current detection circuit 50 in the bias control circuit 40. The detection value is inputted to the computer 20 via an A/D converter 23. The computer 20 controls ON/OFF of the heater 33 of the A/F sensor 30 through the heater control circuit 25. A heater voltage and a heater current according to the ON or OFF of the heater 33 are detected by the heater control circuit 25. Those detection values of heater voltage and heater current are inputted to the computer 20 via an A/D converter 24.

Figure 2:
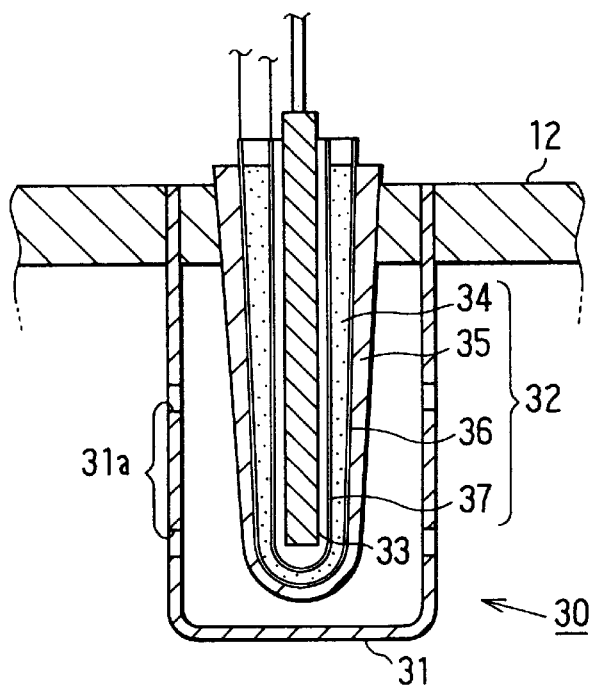
FIG. 2 is a cross sectional view showing an A/F sensor used in the first embodiment.

As shown in FIG. 2, the A/F sensor 30 is provided on the exhaust pipe 12, protruding toward the inside of the exhaust pipe 12. The sensor 30 is constructed by mainly a cover 31, a sensor body 32, and the heater 33. The cover 31 has a U-shape in cross section and a number of small holes 31a for communicating the inside and outside thereof. The sensor body 32 as a sensor element part generates a limit-current corresponding to the concentration of oxygen in a lean air-fuel ratio zone or the concentration of unburned gas (such as CO, HC, and $H_2$) in the rich air-fuel ratio zone.

In the sensor body 32, an exhaust-side electrode layer 36 is firmly attached to the external surface of a solid electrolyte layer 34 formed in a cup shape in cross section and an atmosphere-side electrode layer 37 is firmly attached to the internal surface of the solid electrolyte layer 34. On the outer side of the exhaust-side electrode layer 36, a diffusion resistance layer 35 is formed by a plasma spraying method or the like. The solid electrolyte layer 34 is made of an oxygen ion conducting oxide sintered body which is solid-solved in a material such as $ZrO_2$, $HfO_2$, $ThO_2$, and $Bi_2O_3$ with a material such as CaO, MgO, $Y_2O_3$, and $Yb_2O_3$ used as a stabilizer. The diffusion resistance layer 35 is made of a heat resisting inorganic material such as alumina, magnesia, silica, spinel and mullite. The exhaust-side electrode layer 36 and the atmosphere-side electrode layer 37 are both made of a noble metal with a high catalytic activity such as platinum and have the surfaces to which a porous chemical plating is performed. The area and the thickness of the exhaust-side electrode layer 36 is 10 to 100 $mm^2$ (square millimeters) and about 0.5 to 2.0 $\mu$m, respectively. On the other hand, the area and the thickness of the atmosphere-side electrode layer 36 are 10 $mm^2$ (square millimeters) or larger and about 0.5 to 2.0 $\mu$m.

The heater 33 is housed in the atmosphere-side electrode layer 37 to heat the sensor body 32 (the atmosphere-side electrode layer 37, the solid electrolyte layer 34, the exhaust-side electrode layer 36, and the diffusion resistance layer 35) by its heat generation energy. The heater 33 has a sufficient capacity of generating heat for activating the sensor body 32.

In the A/F sensor 30, the sensor body 32 generates a limit-current according to the concentration of oxygen in a zone leaner than the stoichiometric air-fuel ratio point. In this case, the limit-current corresponding to the concentration of oxygen is determined by the area of the exhaust-side electrode layer 36, and the thickness, the porosity and the average pore diameter of the diffusing resistance layer 35. The sensor body 32 is capable of detecting the concentration of oxygen in accordance with a linear characteristic thereof. Since a high temperature equal to or higher than about 600° C. is required for activating the sensor body 32 and the activating temperature range of the sensor body 32 is narrow, however, the sensor body temperature cannot be controlled in the active zone by heating with only exhaust gas of the engine 10. For this reason, in the present embodiment, the sensor body 32 is heated to the activation temperature zone by controlling the duty ratio of an electric power supply current to the heater 33. In a zone richer than the stoichiometric air-fuel ratio, the concentrations of unburned gases such as carbon monoxide (CO) change almost linearly with the air-fuel ratio and the sensor body 32 generates a limit-current according to the concentration of Co or the like.

Figure 3:
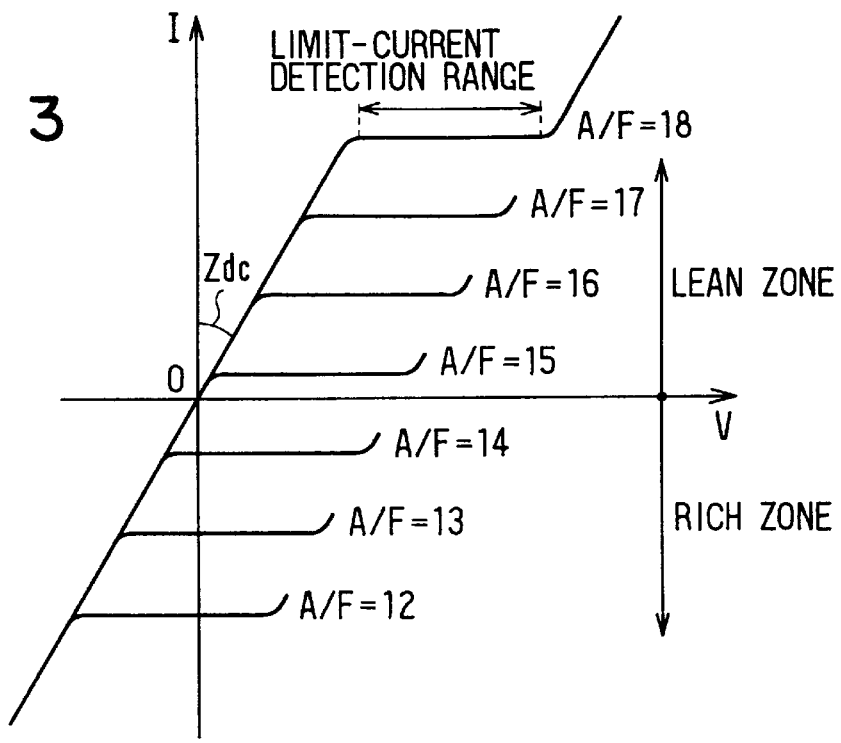
FIG. 3 is a V-I output characteristics of the A/F sensor shown in FIG. 2.

It will be understood from FIG. 3 showing the voltage-current characteristic (V-I characteristics) of the sensor body 32 that a current flowing to the solid electrolyte layer 34 of the sensor body 32, which is proportional to the A/F detected by the A/F sensor 30 and a voltage applied to the solid electrolyte layer 34 have a linear relation. In this case, straight line segments parallel to the voltage axis V constitute a limit-current detection zone which specifies the limit-current of the sensor body 32. Increases and decreases of the limit-current (sensor current) correspond to increases and decreases in the A/F (that is, lean and rich). Specifically, the more the A/F is shifted to the lean side, the more the limit-current increases to. The more the A/F is shifted to the rich side, the more the limit-current decreases to.

In the V-I characteristic, a voltage zone below the straight line segments (limit-current detection zone) parallel to the voltage axis V is a resistance-dominating zone. The gradient of the linear straight line segments in the resistance-dominating zone is specified by the internal resistance (element impedance Zdc) of the solid electrolyte layer 34 in the sensor body 32. Since the element impedance Zdc changes with change in temperature, when the temperature of the sensor body 32 decreases, the gradient is reduced by the increase in Zdc.

Figure 4:
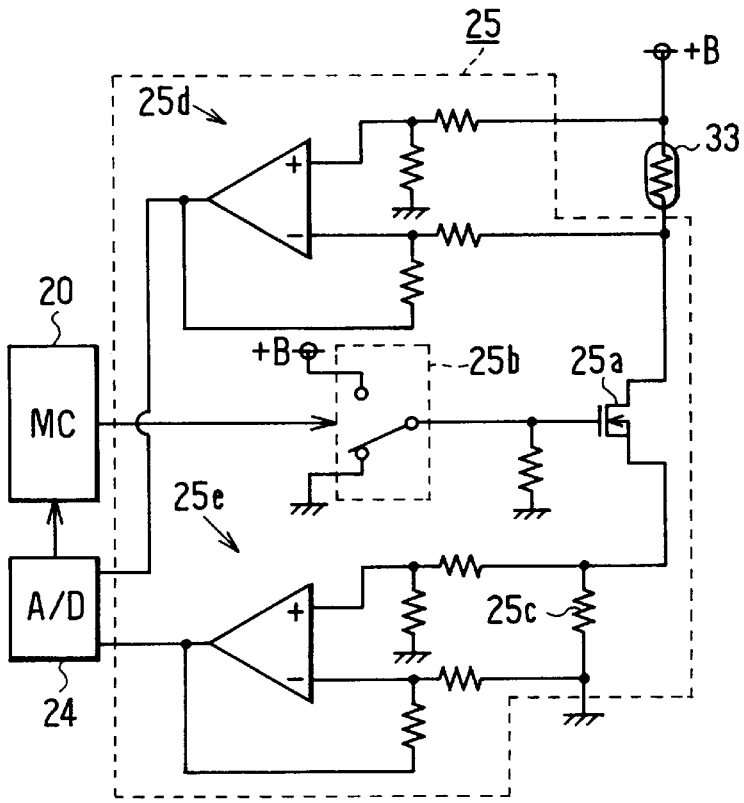
FIG. 4 is a circuit diagram showing a heater control circuit used in the first embodiment.

In the circuit diagram of FIG. 4 showing the heater control circuit 25, one end of the heater 33 is connected to a battery power source +B having the rated 12 volts and the other end is connected to the drain of an n-channel MOS transistor (MOS) 25a used as a semiconductor switching element. The gate of the MOS 25a is connected to a switch 25b which is turned on and off by the computer 20 and the source of the same is connected to the ground via a heater current detecting resistor 25c. A heater voltage Vh is detected by a difference in potentials of both ends of the heater and the detection result is applied to the A/D converter 24 through an operational amplifier 25d. A heater current Ih is detected by a difference in potentials of both ends of the heater current detecting resistor 25c and the detection result is applied to the A/D converter 24 through an operational amplifier 25e.

Figure 5:
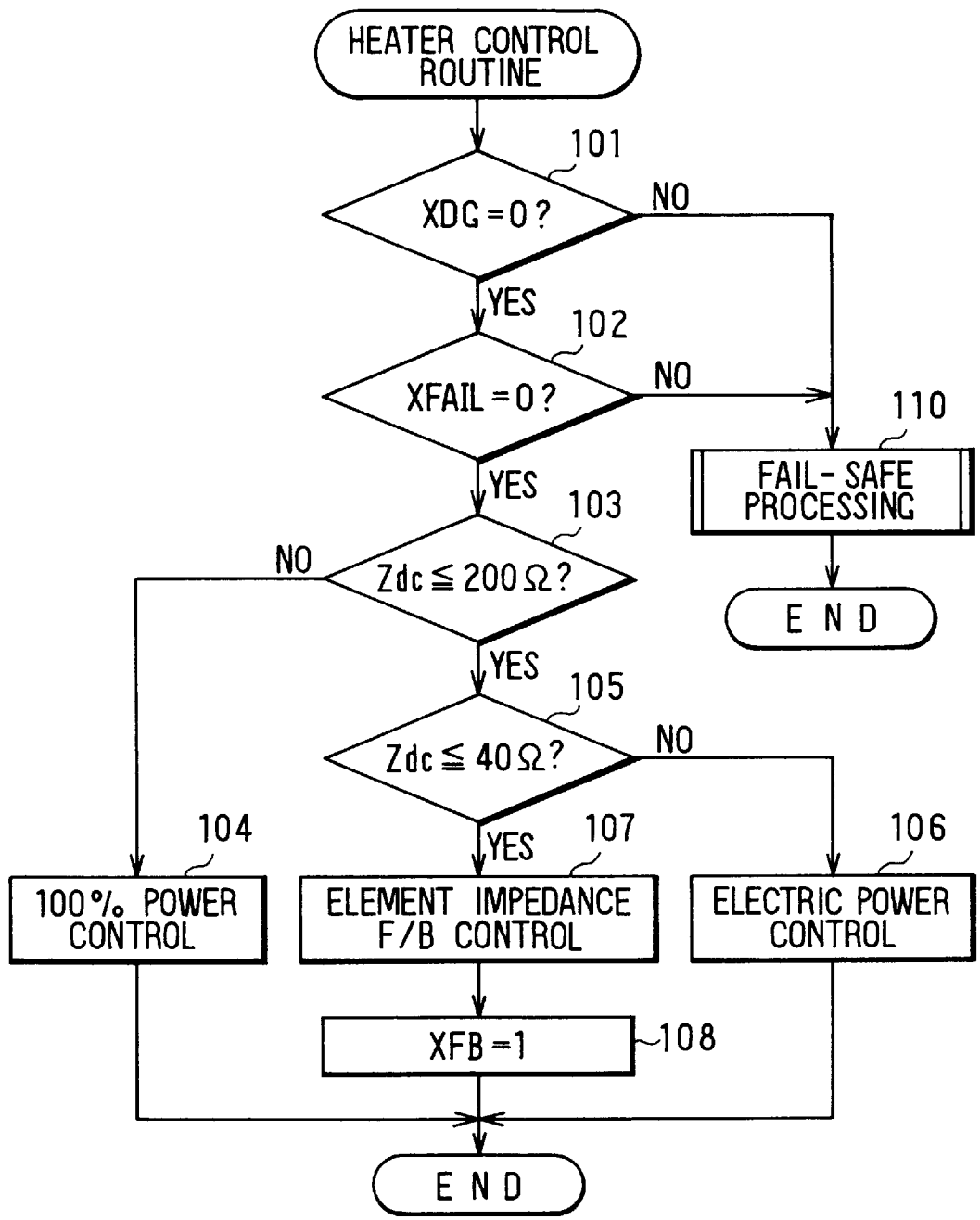
FIG. 5 is a flowchart-showing a heater control routine executed in the first embodiment.
Figure 6:
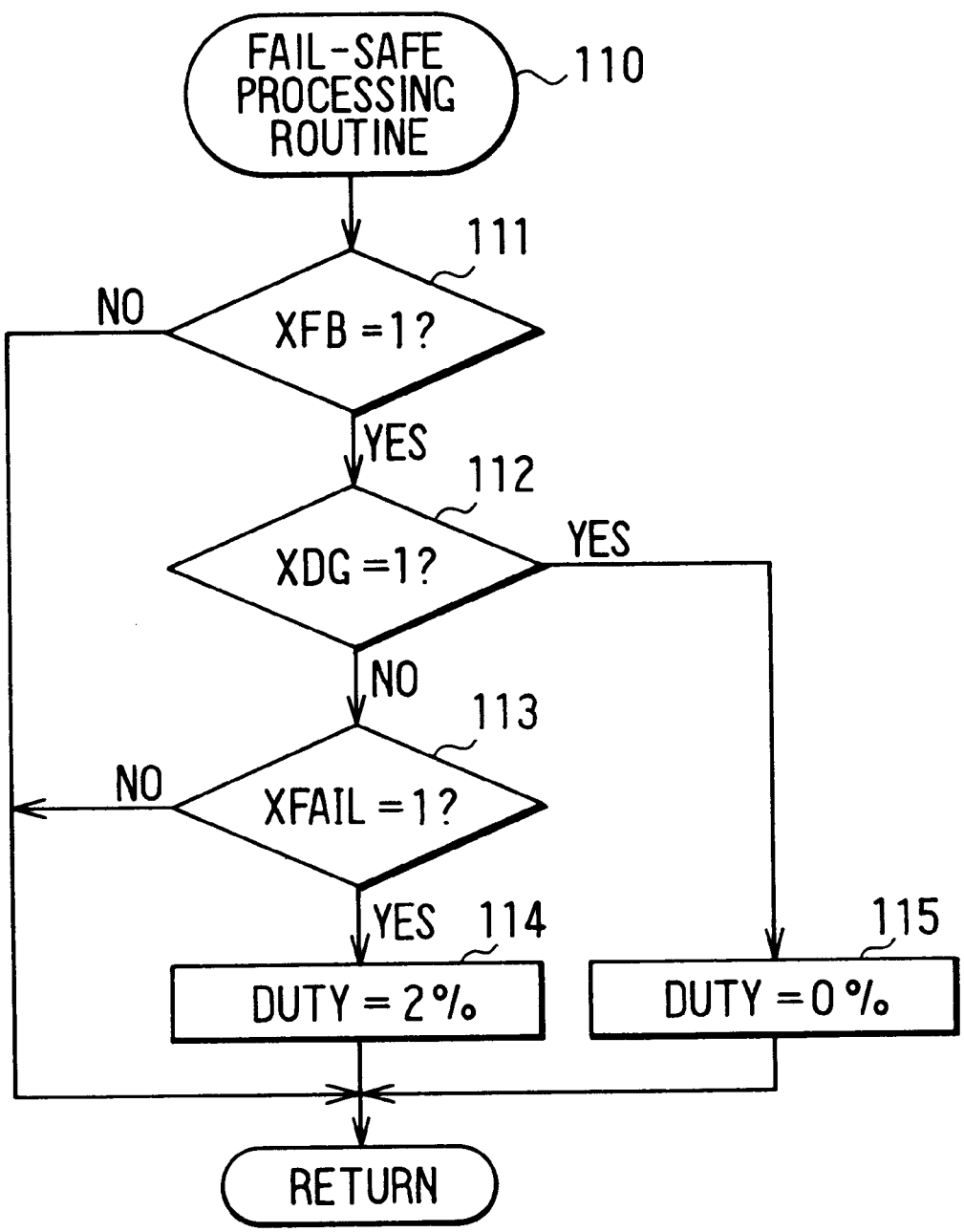
FIG. 6 is a flowchart showing a fail-safe processing routine in the heater control routine shown in FIG. 5.
Figure 7:
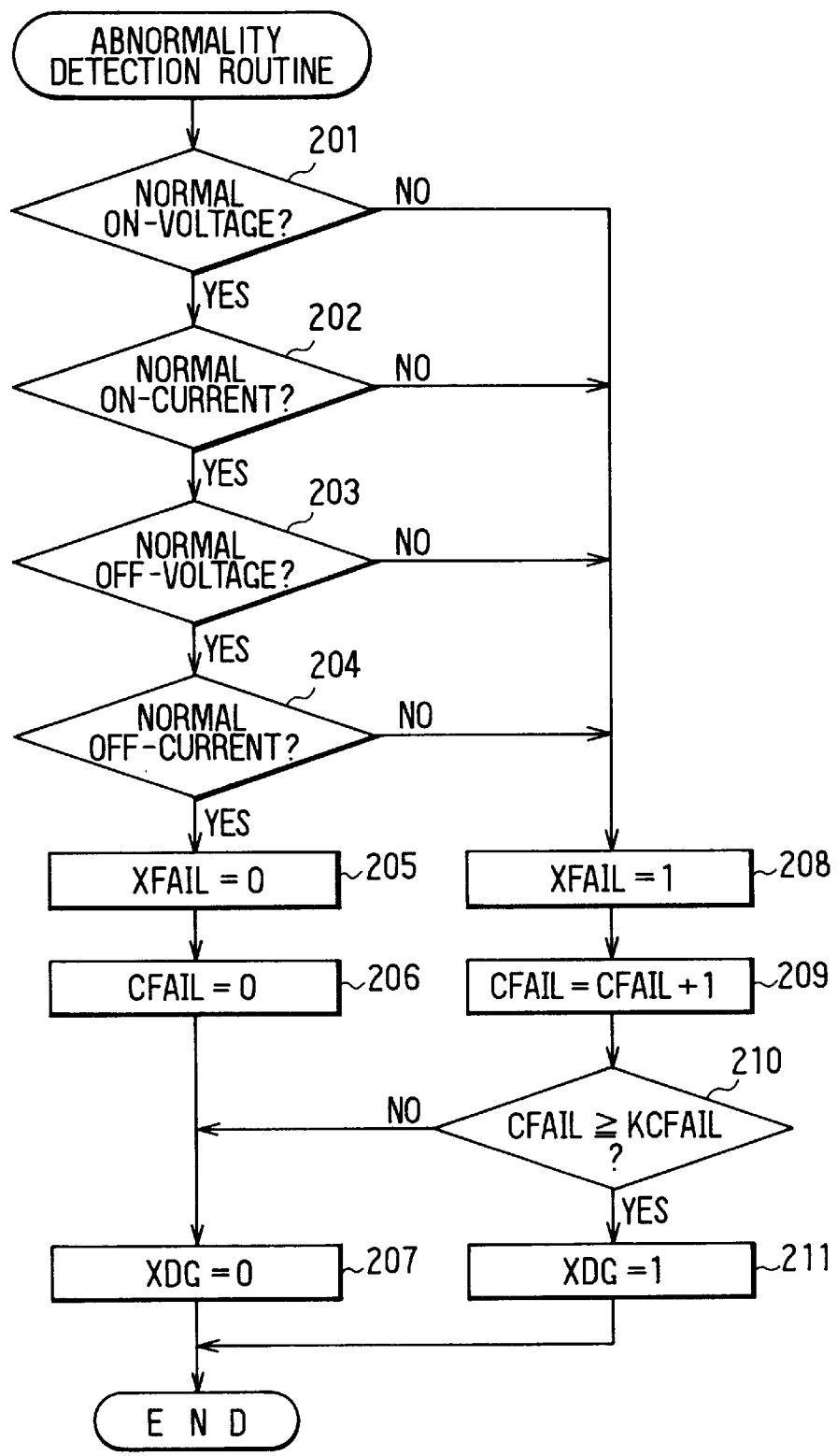
FIG. 7 is a flowchart showing an abnormality detection routine executed in the first embodiment.

The computer 20 is programmed to execute various routines for the heater control shown in FIGS. 5 to 7.

As shown in FIG. 5, the computer 20 determines first at step 101 whether a diagnosis flag XDG is 0 (zero). This flag XDG is used to indicate whether, when an abnormality in the electric power supply to the heater 33 is detected, the detected abnormality is temporary (restorable) or not. XDG=0 and XDG=1 mean that the detected abnormality is temporary and not temporary, respectively. The computer 20 determines at next step 102 whether a power supply abnormality flag XFAIL is 0. This flag XFAIL is set immediately after the detection of abnormality in the power supply to the heater 33. XFAIL=0 and XFAIL=1 mean that the electric power supply is normal and abnormal, respectively. Each of the flags XDG and XFAIL is set and reset in an abnormality detection routine shown in FIG. 7.

The computer 20 proceeds to step 110 with at least one of XDG=1 and XFAIL=1, and executes a fail-safe processing routine shown in FIG. 6. The computer 20 proceeds to step 103 with both XDG=0 and XFAIL=0.

Figure 8:
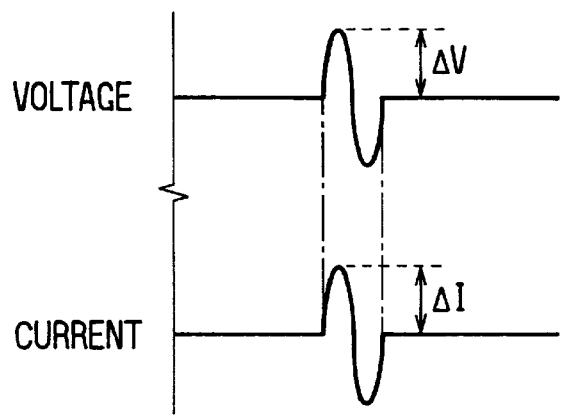
FIG. 8 is a waveform chart showing a process of detecting an element impedance in the first embodiment.

The computer 20 determines at step 103 whether the element impedance Zdc is below a predetermined reference (equal to less than 200 Ω) which is set to determine a semi-activated state of the sensor body 32. Here, the element impedance Zdc may be detected as shown in FIG. 8. That is, the voltage (V) applied to the sensor 30 is changed temporarily in the positive and negative directions to cause a change in the sensor current (I). Either positive or negative changes ΔV and ΔI at this moment are used to detect the element impedance (Zdc=ΔV/ΔI). It is of course possible to detect the element impedance by changes ΔV and ΔI including changes in both positive and negative directions, or by using a sensor current Ineg at the time of applying a negative voltage Vneg (Zdc=Vneg/Ineg).

As the element impedance is high (Zdc>200 Ω) while the engine 10 is still cold, the computer 20 proceeds to next step 104 to perform 100% power control. Under the 100% power control, the heater 33 is supplied with electric power at a 100% duty ratio. This power supply is maintained until the element impedance decreases below 200 Ω by heating.

When the heater 33 heats up and step 103 determines that the heater 33 is heated considerably, the computer 20 then determines at step 105 whether the element impedance Zdc is decreased below another reference (about 40 Ω) which is set to determine a fully-activated state for starting an air-fuel ratio feedback control. The reference 40 Ω is set by adding about 10 Ω to a target impedance 30 Ω.

Figure 9:
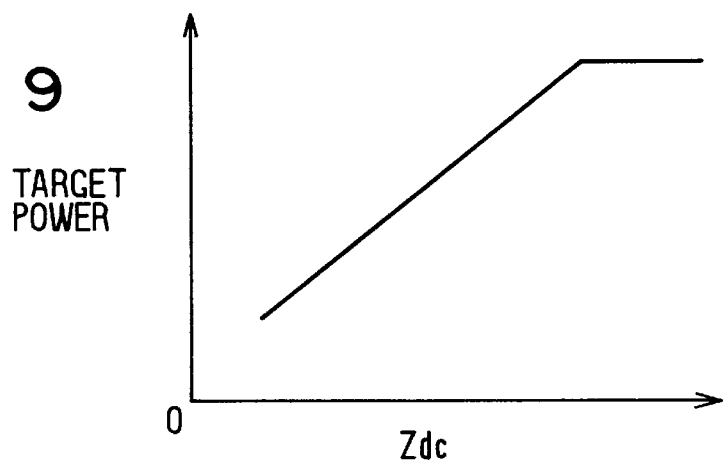
FIG. 9 is a graph showing the element impedance and a target electric power for the heater in the first embodiment.

If step 105 determines that the sensor 30 is not in the fully-activated state, the computer 20 performs a power control at step 106. In this power control, a target power is set in accordance with the detected impedance Zdc as shown in FIG. 9 and the duty ratio of the power supply is determined by the target power.

If step 105 determines that the sensor 30 is activated fully, on the other hand, the computer 20 performs an element impedance feedback control. In this feedback control, a duty ratio DUTY of power supply is calculated as follows by the use of proportional-integral-derivative control calculation.

First, the proportional term GP, integral term GI and derivative term GD are calculated as follows, with KP, KI and KD being proportional constant, integral constant and derivative constant, respectively.

GP=KP×(Zdc−ZdcTG)

GI=GIi−1+KI×(Zdc−ZdcTG)

GD=KD×(Zdc−Zdci−1)

Finally, the duty ratio DUTY is calculated as follows by adding the calculated terms GP, GI and GD.

DUTY=GP+GI+GD

It is to be noted that the duty ratio may be determined by a proportional-integral control calculation or by only a proportional control calculation.

After calculating the duty ratio DUTY at step 107, the computer 20 sets an impedance feedback execution flag XFB (XFB=1) at step 108. The flag XFB is used to indicate whether the feedback (F/B) is being executed. XFB=0 and XFB=1 mean non-execution and execution of the impedance feedback control, respectively. This flag is reset (XFB=0) at the time of starting the engine by an ignition switch (not shown).

In fail-safe processing routine 110 shown in FIG. 6, the computer 20 determines in steps 111 to 113 whether the feedback execution flag XFB, diagnosis flag XDG and abnormality flag XFAIL is 1. If XFB=0 indicating that the feedback control for the element impedance Zdc is not executed, the computer 20 ends this routine 110. If XFB=1, the computer 20 determines at step 112 whether the diagnosis flag XDG is 1. With XDG=1, the computer proceeds to step 115 and set the power supply duty DUTY to the heater 33 to 0% (no power supply).

With XDG=0, the computer determines whether the abnormality flag XFAIL is 1. With XFAIL=1, the computer 20 set the duty DUTY to 2% at step 114. After step 114 or with XFAIL=0, the computer 20 ends this routine 110. As the routine 110 is executed in response to either XDG=1 (step 101) or XFAIL=1 (step 102), the power supply duty DUTY is set to either 0% or 2%.

In the above routine, setting the duty DUTY=2% at step 114 means setting the electric power for the heater 33 to a minimum value required to detect the heater voltage and heater current. In this instance, the heater 33 is considered restorable to normal state even when the abnormality in the heater power supply is detected. As it is likely that the heater 33 is actually in an abnormal state, the power supply period is desirably as short as possible. Setting the duty DUTY=0% at step 115 means stopping the electric power supply to the heater 33. Thus, it becomes impossible to detect the heater voltage and heater current. In this instance, the heater 33 is considered non-restorable from the abnormal state to the normal state.

Referring to FIG. 7 showing the abnormality detection routine, the computer 20 determines at steps 201 to 204 existence/absence of abnormality in the power supply to the heater 33. Specifically, the computer 20 determines; whether ON-voltage of the heater 33 is normal at step 201, whether ON-current of the heater 33 is normal at step 202, whether OFF-voltage of the heater 33 is normal at step 203 and whether OFF-current of the heater 33 is normal at step 202.

Figure 10:
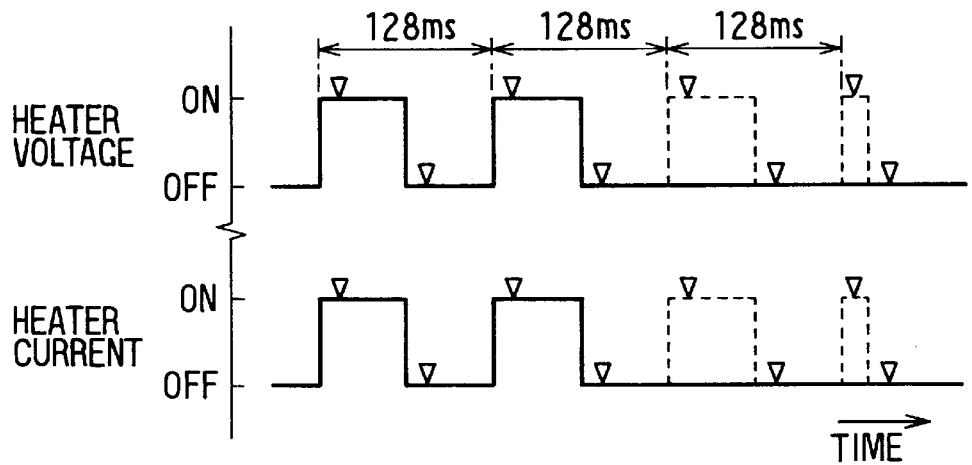
FIG. 10 is a time chart showing a voltage and current of the heater in a normal and abnormal states in the first embodiment.

Here, the ON-voltage, OFF-voltage, ON-current and OFF-current are detected at a fixed period (128 ms) respectively as shown by ∇-mark in FIG. 10. This fixed time period is the same as the time period of executing the abnormality detection routine (FIG. 7). As long as the heater voltages and heater currents correspond to the duty ratio output as shown by the solid line, the electric power supply to the heater 33 is determined normal. However, if the heater voltages and heater currents do not correspond to the duty ratio output as shown by the dotted line, the electric power supply to the heater 33 is determined abnormal.

Provided that all steps 201 to 204 determine that the heater voltages and heater currents are normal, the computer 20 clears the abnormality flag XFAIL, an abnormality counter CFAIL and the diagnosis flag XDG to 0 at steps 205, 206 and 207, respectively, thus ending this routine.

Provided that either one of steps 201 to 204 determines that the heater voltages and heater currents are abnormal, the computer 20 sets the abnormality flag XFAIL to 1 at step 208 and increments the abnormality counter CFAIL by 1 (CFAIL=CFAIL+1) at step 209. The computer 20 then determines whether the count of the abnormality counter CFAIL exceeds a reference KCFAIL (about 5 seconds).

With CFAIL<KCFAIL, the computer 20 proceeds to step 207 to clear the diagnosis (flag XDG=0). With CFAIL≧KCFAIL, the computer 20 proceeds to step 211 to set the diagnosis flag (XDG=1), thus ending the routine.

Figure 11:
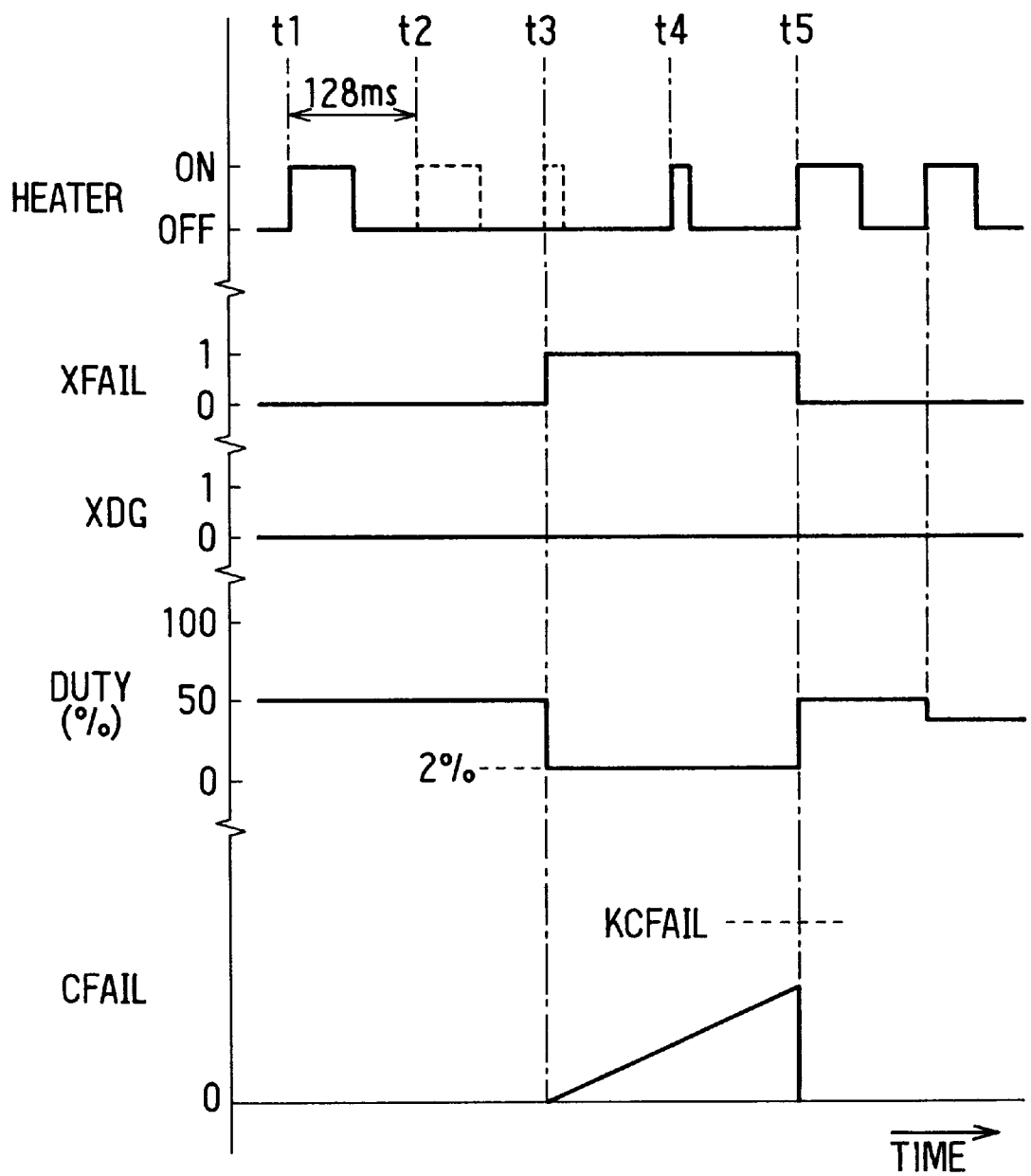
FIG. 11 is a time chart showing a heater control operation in the first embodiment.
Figure 12:
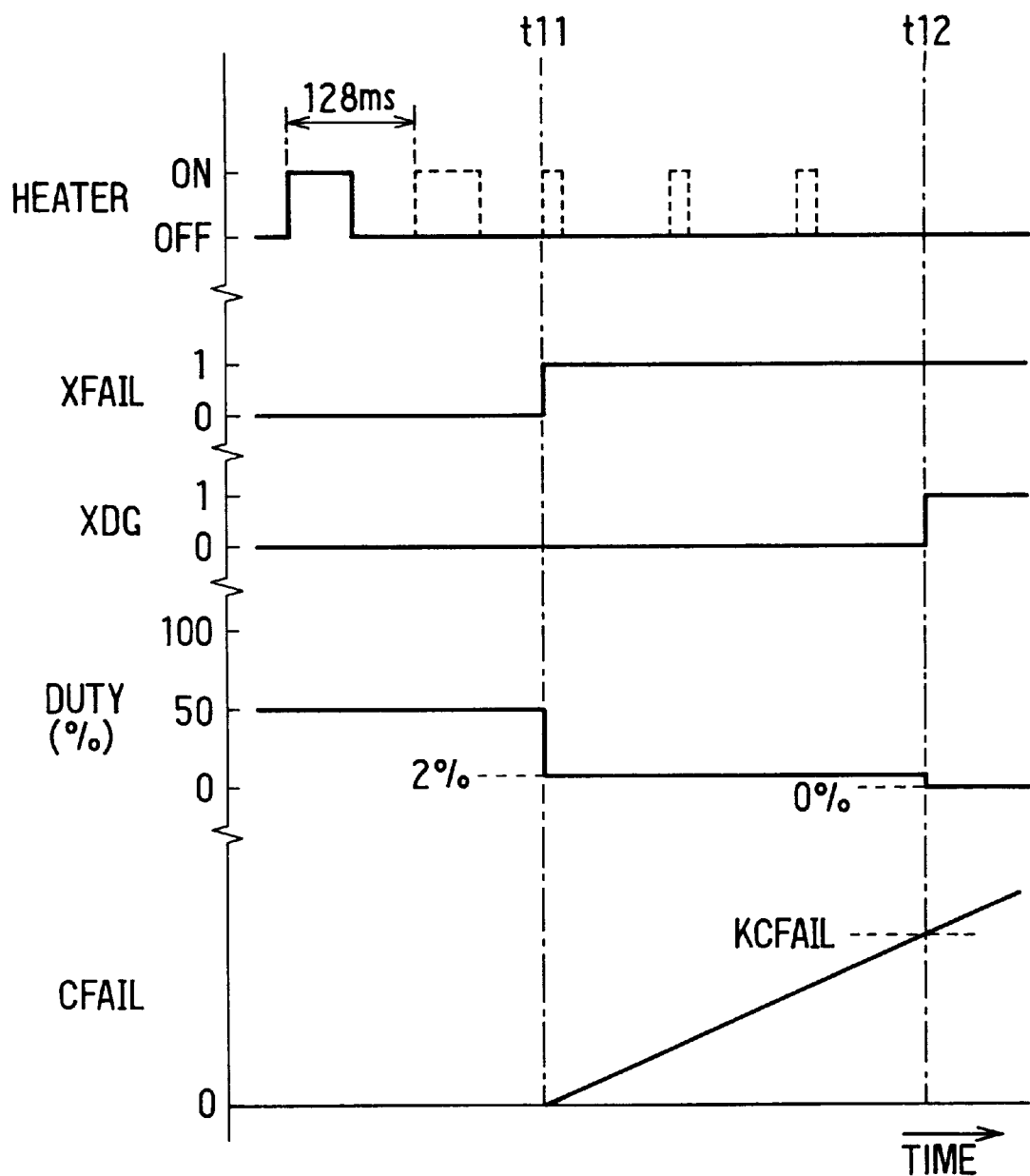
FIG. 12 is a time chart showing another heater control operation in the second embodiment of the present invention.

The above embodiment operates as follows in cases of the detected abnormality of the power supply to the heater 33 being temporary (restorable to normal: FIG. 11) and not temporary (non-restorable to normal: FIG. 12).

Referring to FIG. 11, it is assumed that the heater voltage and heater current corresponding to the duty ratio output DUTY are detected at time t1 but not detected at time t2. When the computer 20 executes the abnormality detection routine (FIG. 7) at time t3 after time t2, the computer 20 sets the abnormality flag (XFAIL=1) and starts incrementing the abnormality counter CFAIL. At this time t3, the power supply duty to the heater 33 is changed to DUTY=2% in response to setting the abnormality flag (XFAIL=1).

Provided that the abnormality disappears before time t4, the heater voltage and current are detected as corresponding to the duty ratio (DUTY=2%). As a result, the abnormality is determined to have been temporary and restored to the normal state. Thereafter, at time t5, the abnormality flag is reset (XFAIL=0) and the abnormality counter is cleared (CFAIL=0). At this time, the duty ratio DUTY is returned to the target duty ratio for the element impedance feedback control.

In the above operation, as the count of the abnormality counter CFAIL does not attain the reference KCFAIL, the diagnosis flag is never set to XDG=1. That is, even when the power supply to the heater 33 becomes abnormal for a short period of time, it becomes possible to restore the normal state.

Referring next to FIG. 12, it is assumed that the power supply to the heater 33 is detected as abnormal at t11. The computer 20 sets the abnormality flag (XFAIL=1) and starts incrementing the abnormality counter CFAIL. At this time t11, the power supply duty to the heater 33 is changed to DUTY=2% in response to setting the abnormality flag (XFAIL=1).

Provided that the abnormality continues to exist, the abnormality counter CFAIL continues its incrementing operation. When the count of the abnormality counter CFAIL reaches the reference KCFAIL at time t12, the diagnosis flag is set (XDG=1) and the power supply duty DUTY is changed to 0%. The diagnosis flag XDG=1 disables return of the power supply to the heater 33 from the abnormal state to the normal state.

It is to be understood in this operation that the oxygen responsive element of the A/F sensor 30 will be maintained at about 400° C.–500° C. by the high temperature exhaust gas from the engine 10, even under the condition that the power supply to the heater 33 is stopped (DUTY=0%) in response to the continuing abnormality in the heater power supply. Thus, the A/F sensor 30 is maintained in the semi-activated state under which it is impossible to detect the air-fuel ratio of mixture supplied to the engine 10 accurately by the use of the limit current. However, it is still possible to detect whether the air-fuel ratio of mixture supplied to the engine 10 is richer or leaner than the stoichiometric ratio. Therefore, it is possible to continue the air-fuel ratio feedback control to the stoichiometric ratio by the output of the A/F sensor 30. That is, the air-fuel ratio feedback control can be maintained as long as the A/F sensor 33 is operative in spite of the continuing abnormality of the heater 33.

The above embodiment provides the following advantages.

(a) It is determined not only whether the heater power supply is abnormal and whether it has restored its normal operation. Therefore, even when the abnormality in the heater power supply occurs temporarily, the heater power supply can be restored to activate the A/F sensor 30 immediately after the temporary abnormality.

(b) The duty ratio of the power supply to the heater 33 is changed to the minimum ratio (2%) by which the heater voltage or heater current can still be detected. This enables determination of the restoration of the normal power supply after the temporary abnormality. Provided that the abnormality continues further during the period of the minimum power supply, the power supply to the heater 33 can be stopped to protect the A/F sensor 30.

(c) The determination period of the restoration to the heater 33 is limited to the predetermined period (KCFAIL) after the detection of the abnormality. Thus, unnecessary continuation of the minimum power supply can be reduced to a minimum.

Second Embodiment

Figure 13:
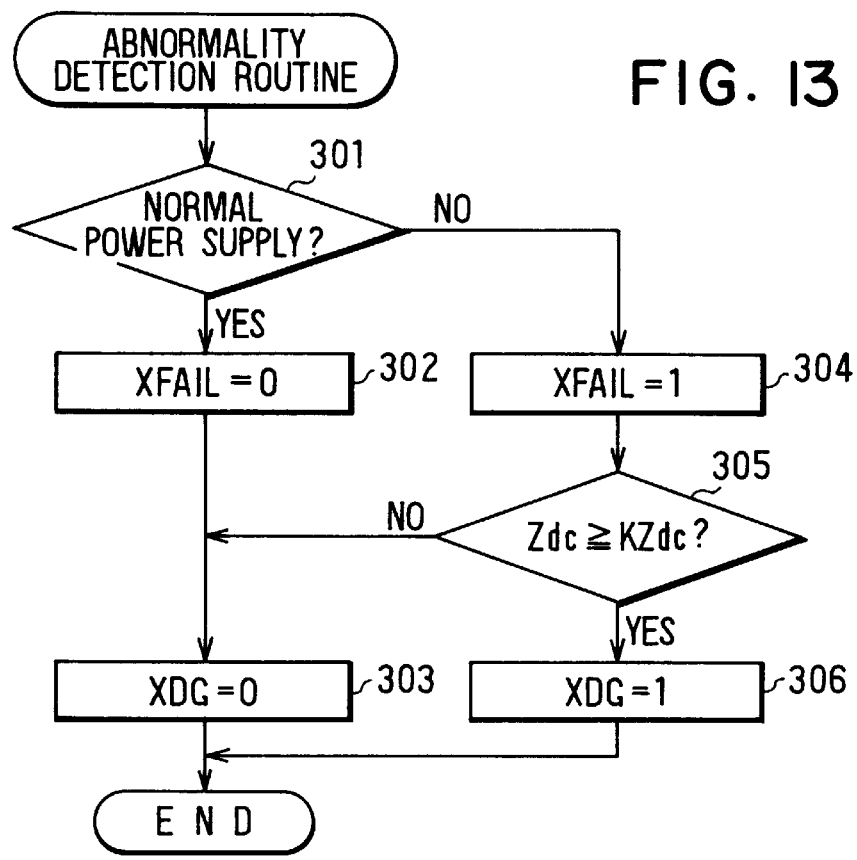
FIG. 13 is a flowchart showing another abnormality detection routine executed in the second embodiment.

In the second embodiment shown in FIG. 13, the abnormality detection routine (FIG. 7) is executed as shown in FIG. 13, with other controls being the same as in the first embodiment. That is, the computer 20 first determines at step 301 whether the heater power supply is normal. This determination may be implemented as in steps 201 to 204 (FIG. 7). As long as the heater power supply is normal, the computer 20 clears the abnormality flag (XFAIL=0) and the diagnosis flag (XDG=0) at steps 302 and 303, respectively.

Provided that the abnormality occurs in the heater power supply operation, the computer 20 sets the abnormality flag (XFAIL=1) at step 304 and proceeds to step 305 to determine whether the element impedance Zdc is in excess of a reference KZdc. This step 305 is for detecting drop of the element temperature which may be caused by signal wire disconnection in the heater system, for instance. If the element impedance is lower than the reference KZdc, the computer 20 clears the diagnosis flag (XDG=0) at step 303. If it is higher than the reference KZdc, on the other hand, the computer sets the diagnosis flag XDG (XDG=1) at step 306.

Thus, in the second embodiment also, the detection of the abnormality by the reduced heater power supply (DUTY=2%) is maintained to determine if the detection of abnormality is temporary. Further, as it is limited to the certain period, unnecessary continuation of the heater power supply is stopped.

Modification

In the above embodiments, detection of the abnormality in the heater power supply shown in FIGS. 7 and 13 may be modified. For instance, the abnormality may be detected by only ON-voltage and OFF-voltage or ON-current and OFF current of the heater 33. alternatively, it may be detected by a change in the electric power actually supplied to the heater 33 (heater voltage×heater current) relative to a change in the power supply duty ratio.

Figure 14:
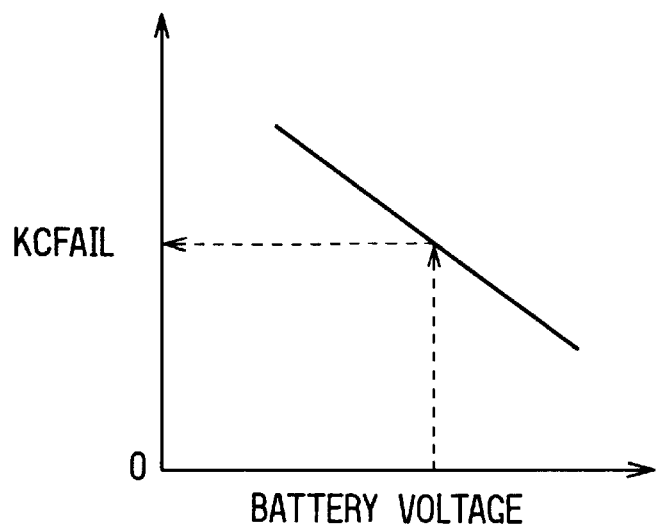
FIG. 14 is a graph showing a relation between a battery voltage and a determination reference in the second embodiment.

In the abnormality detection routine in the first embodiment (FIG. 7), the reference KCFAIL in step 210 may be set variably. That is, as shown in FIG. 14, the reference KCFAIL may be set to vary in accordance with a battery voltage so that the reference KCFAIL increases as the battery voltage decreases. According to this setting of the reference KCFAIL, even when the temporary abnormality occurs frequently due to drop of the battery voltage, restoration to the normal power supply can be attained appropriately. The battery voltage to be used for setting the reference KCFAIL variably may be replaced by other parameters which may cause changes in the heater power supply.

It is also possible to set variably the reference KZdc used in the second embodiment (step 305 in FIG. 13) in the similar manner.

The references KCFAIL (step 210) and KZdc (step 305) may be eliminated so that the restoration to the normal heater power supply may be determined without time limitation.

The above embodiments may be applied to systems using other types of gas concentration sensors as long as an electric heater is used for activating a gas sensing element.

The present invention should not be limited to the modified further without departing from the spirit of the present invention.

What is claimed is:

1. An apparatus for controlling an electric power supply to a heater of a gas concentration sensor, the apparatus comprising:

power supply means for supplying electric power to a heater of a gas concentration sensor;

abnormality detection means for detecting an abnormality in the heater;

means for controlling said power supply means to supply power to said heater after an abnormality in the heater is detected; and restoration determination means for determining restoration of said heater to a normal state after a detection of the abnormality.

2. The apparatus of claim 1, further comprising:

fail-safe processing means for reducing after a detection of the abnormality a time period of supplying the electric power to a minimum period required to detect at least one of a voltage and a current of the heater.

3. The apparatus of claim 2, wherein:

said power supplying means supplies power at a reduced level after an abnormality in the heater is detected and before the restoration determining means determines restoration of the heater and wherein the restoration determination means detects the at least one of the voltage and the current of the heater during said supply of the reduced electric power and determines the restoration of the heater to the normal state when a detected value of the voltage and the current is normal.

4. The apparatus of claim 1, further comprising:

limitation means for limiting a determination of the restoration under a predetermined condition.

5. The apparatus of claim 4, wherein:

the predetermined condition is a lapse of a predetermined time after the detection of the abnormality.

6. The apparatus of claim 4, wherein:

the predetermined condition is an increase in an impedance of the gas concentration sensor above a predetermined impedance.

7. The apparatus of claim 1, further comprising:

fail-safe processing means for reducing after a detection of the abnormality the electric power supplied to the heater to a minimum power required to detect an operativeness of the heater, wherein the gas concentration sensor is disposed in an exhaust pipe of an engine to detect an oxygen concentration.

8. The apparatus of claim 7, further comprising:

the restoration determination means detects the operativeness of the heater during the supply of the reduced electric power and changes from a supply of the reduced electric power to a supply of a normal electric power when the operativeness is detected during the supply of the reduced electric power.

9. The apparatus of claim 8, further comprising:

limitation means for limiting a determination of the operativeness of the heater to a predetermined time, said predetermined time being dependent upon and variable with a battery voltage after the detection of the abnormality; and stop means for stopping the supply of the electric power in the absence of detection of operativeness of the heater during the predetermined period.

10. The apparatus of claim 8, further comprising:

limitation means for limiting the supply of the reduced electric power to a period in which an impedance of the gas concentration sensor is below a predetermined impedance.

11. The apparatus of claim 1, wherein the restoration determination means determines the restoration while said heater is supplied with electric power in a mode different than that supplied when the abnormality was detected.

12. The apparatus of claim 1, wherein said restoration determining means determines whether the detected abnormality was temporary and when the abnormality is determined to have been temporary, restores the heater to a normal operating state.

13. A method of controlling an electric power supply to a heater of an oxygen concentration sensor disposed in an exhaust of an engine, the method comprising the steps of:

supplying a normal electric power to a heater of an oxygen concentration sensor;

detecting an abnormality in the heater;

reducing the electric power from the normal electric power in response to a detection of the abnormality and supplying the reduced electric power to said heater after said abnormality is detected;

determining whether the detected abnormality of said heater discontinues during said supply of the reduced electric power; and restoring the electric power supply to said heater from the reduced electric power to the normal electric power after a determination of discontinuation of the abnormality of said heater.

14. The method of claim 13, further comprising:

limiting at least one of the determining step and a period of the power reducing step to a predetermined time; and stopping a power supply to the heater when the predetermined time elapses in the absence of a determination of discontinuation of the abnormality.

15. The method of claim 14, further comprising:

varying the predetermined time according to a battery voltage.

16. The method of claim 13, further comprising:

limiting the power reducing step to a period in which an impedance of the oxygen concentration sensor is below a predetermined impedance; and stopping a power supply to the heater when the impedance of the oxygen concentration sensor increases above the predetermined impedance.

17. The method of claim 13, wherein:

the detecting step and the determining step compares at least one of an actual voltage and an actual current of the oxygen concentration sensor with a respective desired value.

18. A method of controlling an electric power supply to a heater of a gas concentration sensor, comprising:

supplying electric power to a heater of a gas concentration sensor;

detecting an abnormality in the heater by determining whether at least one of a heater voltage and a heater current is abnormal;

supplying power to said heater after an abnormality is detected in said heater;

determining whether said at least one abnormal heater voltage or abnormal heater current is temporary; and when said detected abnormality is determined to be temporary, restoring said heater to a normal state.

19. A method as in claim 18, wherein said step of restoring the heater to a normal state comprises supplying the electric power at a mode corresponding to that supplied before the abnormality was detected.

20. A method as in claim 18, wherein said step of supplying power after an abnormality is detected comprises supplying power at a reduced level to said heater.

* * * * *